United States Patent
Stolka et al.

(10) Patent No.: US 9,436,993 B1
(45) Date of Patent: Sep. 6, 2016

(54) SYSTEM AND METHOD FOR FUSED IMAGE BASED NAVIGATION WITH LATE MARKER PLACEMENT

(71) Applicant: CLEAR GUIDE MEDICAL, INC., Baltimore, MD (US)

(72) Inventors: Philipp Jakob Stolka, Baltimore, MD (US); Ehsan Basafa, Baltimore, MD (US); Pezhman Foroughi, Towson, MD (US); Gregory Donald Hager, Baltimore, MD (US); Emad Mikhail Boctor, Baltimore, MD (US)

(73) Assignee: Clear Guide Medical, Inc, Baltimore, MD (US)

( * ) Notice: Subject to any disclaimer, the term of this patent is extended or adjusted under 35 U.S.C. 154(b) by 0 days.

(21) Appl. No.: 14/689,849

(22) Filed: Apr. 17, 2015

(51) Int. Cl.
*G06K 9/00* (2006.01)
*G06T 7/00* (2006.01)
*G06T 5/00* (2006.01)

(52) U.S. Cl.
CPC ......... *G06T 7/0012* (2013.01); *G06K 9/00771* (2013.01); *G06T 5/001* (2013.01); *G06T 7/0024* (2013.01); *G06T 7/0081* (2013.01); *G06T 2207/10016* (2013.01); *G06T 2207/30204* (2013.01)

(58) Field of Classification Search
None
See application file for complete search history.

(56) References Cited

U.S. PATENT DOCUMENTS

| 8,880,151 | B1 | 11/2014 | Stolka et al. | |
| 2005/0182295 | A1* | 8/2005 | Soper | A61B 1/0008 600/117 |
| 2013/0016185 | A1 | 1/2013 | Stolka et al. | |
| 2013/0216114 | A1* | 8/2013 | Courtney | A61B 5/0066 382/130 |
| 2014/0044325 | A1* | 2/2014 | Ma | G06T 7/0028 382/128 |
| 2015/0182191 | A1* | 7/2015 | Caluser | A61B 5/4312 600/440 |

OTHER PUBLICATIONS

Arun et al. "Least-Squares Fitting of Two 3-D Point Sets", IEEE Transactions on Pattern Analysis and Machine Intelligence, 1987, vol. PAMI-9, No. 5, pp. 698-700.
Besl et al., "A Method for Registration of 3-D Shapes", IEEE Transactions on Pattern Analysis and Machine Intelligence, vol. 14, No. 2, 1992, pp. 239-256.
Boctor et al., "Ultrasound Monitoring of Tissue Ablation via Deformation Model and Shape Priors", International Conference on Medical Image Computing and Computer-Assisted Intervention, MICCAI 2006, LNCS 4191, pp. 405-412.
Hager et al., "The XVision System: A General-Purpose Substrate for Portable Real-Time Vision Applications", in Computer Vision and Image Understanding, 1998, vol. 69, No. 1, pp. 23-37.
Olson: "AprilTag: A robust and flexible visual fiducial system", IEEE ICRA 2011, pp. 1-8.

(Continued)

*Primary Examiner* — Shervin Nakhjavan
(74) *Attorney, Agent, or Firm* — Venable LLP; Henry J Daley

(57) ABSTRACT

Systems and methods for image guidance, which may include an image processing unit, cameras, and handheld real-time imaging components or handheld displays, wherein the cameras observe visual features on patients, tools, or other components, and wherein said features allow camera or object positions to be determined relative to secondary image data or a reference position, and wherein the image processing unit is configured to dynamically register observations with secondary image data, and to compute enhanced images based on combinations of one or more of secondary image data, positioning data, and real-time imaging data.

31 Claims, 11 Drawing Sheets

(56) References Cited

OTHER PUBLICATIONS

Rivaz et al., "Ablation monitoring with elastography: 2D in-vivo and 3D ex-vivo studies", International Conference on Medical Image Computing and Computer-Assisted Intervention, MICCAI, 2008, LNCS 5242, pp. 458-466.

Rivaz et al., "Tracked Regularized Ultrasound Elastography for Targeting Breast Radiotherapy", Medical Image Computing and Computer Assisted Intervention, MICCAI, 2009, LNCS 5761, pp. 507-515.

Stolka et al. "Navigation with local sensors in handheld 3D ultrasound: initial in-vivo experience", SPIE Medical Imaging 2011, pp. 1-9.

Wang et al. "The Kinect as an interventional tracking system:" SPIE Medical Imaging, International Society for Optics and Photonics, 2012, pp. 83160U-83160U.

* cited by examiner

SYSTEM AND METHOD FOR FUSED IMAGE BASED NAVIGATION WITH LATE MARKER PLACEMENT

BACKGROUND

1. Field of Invention

The field of the currently claimed embodiments of this invention relates to imaging devices, and more particularly to imaging devices with one or more sensors for observation and tracking of a patient and one or more tools.

2. Discussion of Related Art

In image-guided interventions, the tracking and localization of imaging devices and medical tools during procedures is exceptionally important and considered the main enabling technology in image-guided surgery (IGS) systems. Most tracking technologies may be categorized into the following groups: 1) mechanical-based tracking including active robots (e.g., DaVinci robot) and passive-encoded mechanical arms (e.g., Faro mechanical arms), 2) optical-based tracking, 3) acoustic-based tracking, and 4) electromagnetic (EM)-based tracking.

Ultrasound is one useful imaging modality for image-guided interventions including ablative procedures, biopsy, radiation therapy, and surgery. In the literature and in research labs, ultrasound-guided intervention research is performed by integrating a tracking system (either optical or EM methods) with an ultrasound (US) imaging system to, for example, track and guide liver ablations, or in external beam radiation therapy [E. M. Boctor, M. DeOliviera, M. Choti, R. Ghanem, R. H. Taylor, G. Hager, G. Fichtinger, "Ultrasound Monitoring of Tissue Ablation via Deformation Model and Shape Priors", International Conference on Medical Image Computing and Computer-Assisted Intervention, MICCAI 2006; H. Rivaz, I. Fleming, L. Assumpcao, G. Fichtinger, U. Hamper, M. Choti, G. Hager, and E. Boctor, "Ablation monitoring with elastography: 2D in-vivo and 3D ex-vivo studies", International Conference on Medical Image Computing and Computer-Assisted Intervention, MICCAI 2008; H. Rivaz, P. Foroughi, I. Fleming, R. Zellars, E. Boctor, and G. Hager, "Tracked Regularized Ultrasound Elastography for Targeting Breast Radiotherapy", Medical Image Computing and Computer Assisted Intervention (MICCAI) 2009]. Current commercial systems may include integrating an EM tracking device into high-end cart-based US system. Small EM sensors may be integrated into the ultrasound probe, and similar sensors may be attached and fixed to the intervention tool of interest.

Limitations of the current approach on both the research and commercial sides may be attributed to the available tracking technologies and to the feasibility of integrating these systems and using them in clinical environments. For example, mechanical-based trackers are considered expensive and intrusive solutions, i.e. they require large space and limit user motion. On the other hand, acoustic tracking does not provide sufficient navigation accuracy. Optical and EM tracking technologies require intrusive setups with a base camera (in case of optical tracking methods) or a reference EM transmitter (in case of EM methods). Additionally, optical rigid-body or EM sensors have to be attached to the imager and all needed tools, hence offline calibration and sterilization steps are required. Furthermore, none of these systems natively assist multi-modality fusion registration (e.g. between pre-operative CT/MRI plans and intra-operative ultrasound), and do not contribute to direct or augmented visualization either. Thus, there remains a need for improved combined imaging and registration devices for use in image-guided surgery.

SUMMARY

Aspects of the invention may include systems, tools, and methods.

In some embodiments of the invention, a system for medical image guidance may be provided. The system may include an image processing system, one or more cameras, a display, and may make use of secondary image data and observations of visible features on a patient surface and tools. In that system, the display may be configured to display enhanced images derived from secondary image data and observations and based on relative positions of one or more of cameras, display, patient, and tools as determined by the image processing system by computing registrations and tracking information between secondary image data, cameras, patient, and tools. Different combinations of markers present in secondary image data, markers attached before the medical intervention, and markers observed by the cameras may be used to sequentially compute said registrations and tracking information.

In yet another embodiment, a method for medical image guidance may be presented. The method may include receiving, by the image processing system, from one or more cameras, input observations which may include images of one or more of patients, artificial markers, natural features, and interventional tools, wherein the markers may be self-identifying or multi-modality markers; calculating, based on the observations, relative positions between currently and previously observed entities; calculating, based on determined positions, registrations between entities; and displaying enhanced images derived from one or more of real-time imaging data, secondary image data, and observations and based on relative positions of display, patient, and tools as determined by the image processing system. The method may further include calculating, based on the observations, relative deformations between currently and previously observed surface features; calculating, based on the estimated surface deformations, deformations of the secondary image data; and displaying enhanced images derived from one or more of deformed secondary image data and real-time imaging data, as determined by the image processing system.

BRIEF DESCRIPTION OF THE DRAWINGS

Further objectives and advantages will become apparent from a consideration of the description, drawings, and examples.

DETAILED DESCRIPTION

Figure 1:
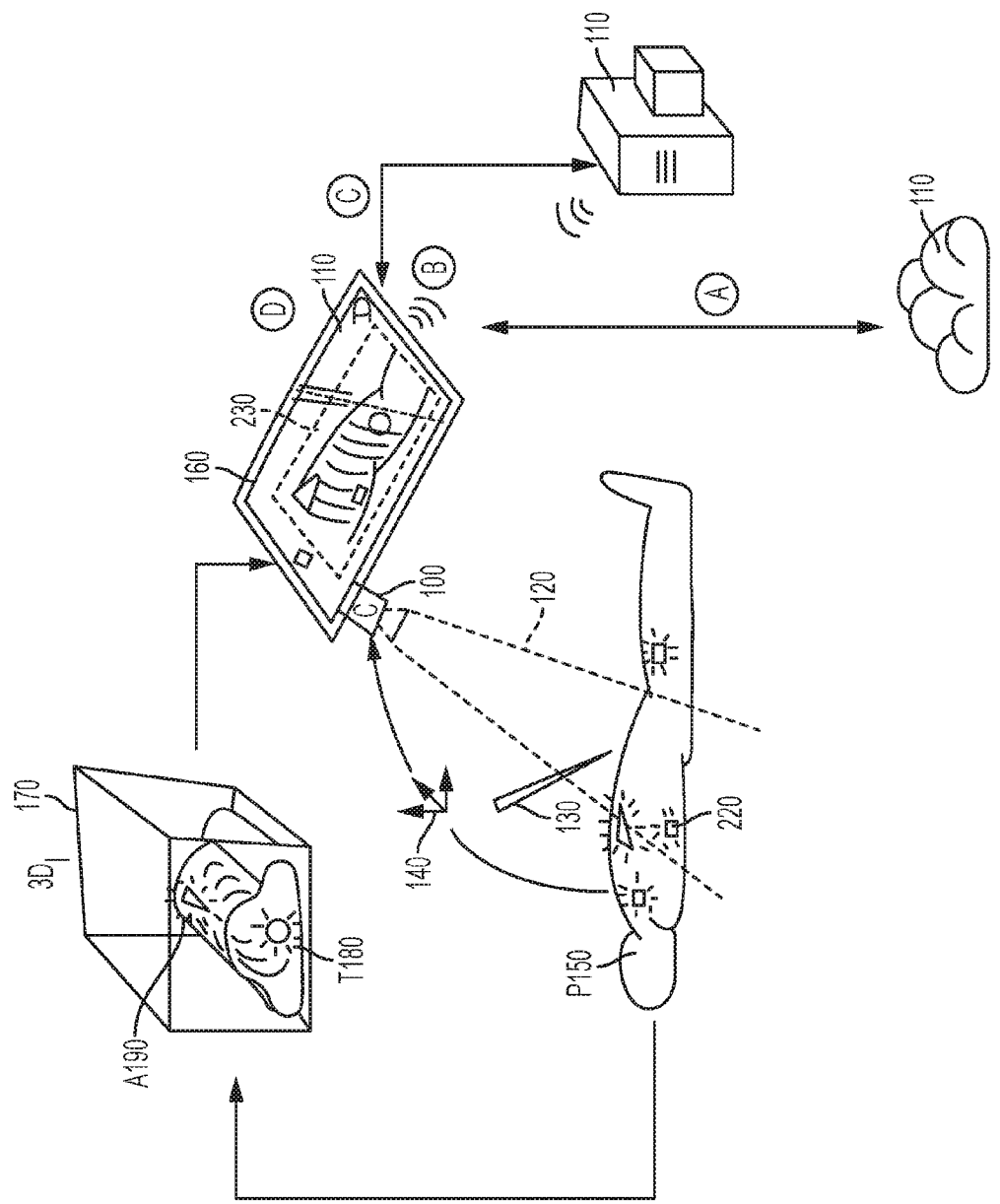
FIG. 1 shows an embodiment of an imaging system according to an embodiment of the current invention.

Embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of this invention take the form of IGI-(image-guided interventions)-enabling "platform technology." This technology simultaneously overcomes the limitations of tracking, registration, visualization, and guidance by integrating techniques related to needle identification and tracking using computer vision; multi-modality registration with novel combinations of orthogonal imaging modalities; and imaging device tracking using local sensing approaches; among others. Examples of IGI may be seen in U.S. patent application Ser. No. 13/511,101, titled "Low-cost image-guided navigation and intervention systems using cooperative sets of local sensors," published as U.S. Patent Application Publication No. 2013/0016185, the contents of which are incorporated herein incorporated by reference in their entirety.

The current invention covers a wide range of different embodiments, sharing a tightly integrated common core of components and methods used for general imaging, vision, and local sensing.

Some embodiments of the current invention are directed to combining a group of complementary technologies to provide a local sensing approach that can enable tracking of medical imaging devices, for example, with the potential to significantly reduce errors and increase positive patient outcomes. This approach can provide a platform technology for the tracking of displays, ultrasound probes, or other imaging devices, intervention guidance, or information visualization according to some embodiments of the current invention. By combining real-time optical imaging with image analysis algorithms and independent optical-inertial sensors, according to some embodiments of the current invention, it is possible to incrementally track the current motion and thus reconstruct the position and trajectory of displays, patients, surgical needles, and other tools or objects, all of which may also be registered to different imaging modalities based on this tracking data.

Some embodiments of the current invention allow the segmentation and tracking of surfaces, markers, needles, and other tools (using visual, ultrasound, and/or other imaging and localization modalities), allowing for example the integration into a complete tracked, image-guided intervention system.

Some embodiments of the current invention allow imaging procedures with improved sensitivity and specificity as compared to the current state of the art. This can open up several possible application scenarios that previously required harmful X-ray/CT or expensive MRI imaging, external tracking, expensive, imprecise, time-consuming, or impractical hardware setups, or combinations of these, and approaches that were simply afflicted with an inherent lack of precision and guarantee of success, such as: biopsies, RF/HIFU ablations etc., 2D- or 3D-ultrasound-based needle placement, brachytherapy, other applications relying on tracked imaging and tracked tools, or even interventions performed without imaging, such as anaesthesiological needle placements for nerve blocks or epidurals.

Embodiments of the current invention provide several advantages over existing technologies, such as combinations of: immediate US-to-CT/MRI registration (no need for tedious acquisition of US volumes or for precise demonstration of markers), immediate CT/MRI registration to the patient, low-cost tracking of patients, tools, and displays, reduced need for repeated imaging, and direct visualization of instruments and targets on the patient anatomy. The invention allows for local, compact, and non-intrusive solutions, i.e. ideal tracking systems for hand-held and compact ultrasound systems, but also for CT, MRI, fluoro, or CBCT systems that are primarily used in intervention and point-of-care clinical suites, as well as for general needle/tool tracking in other interventional settings.

For example, some embodiments of the current invention are directed to devices and methods for the tracking of ultrasound probes, displays, or other imaging devices. By combining handheld imaging with image analysis algorithms and cameras mounted on-probe, on-display, or separately, it is possible to reconstruct the position and trajectory of tools (e.g., surgical tools, surgical needles, etc.), patients, displays, and other objects by incrementally tracking their current motion according to an embodiment of the current invention. This can enable several possible application scenarios such as ultrasound-based 3D needle guidance or dynamic reprojection of static image data using tracked displays showing real-time DRRs or other visualizations that previously required expensive, imprecise, or impractical hardware setups.

Current sonographic procedures mostly use handheld 2D ultrasound (US) probes that return planar image slices through the scanned 3D volume (the "region of interest" (ROI)). For percutaneous interventions requiring tool guidance, prediction of the tool trajectory is often based on tracking sensors attached to the distal (external) tool end and/or on mental extrapolation of the trajectory, relying on the operator's experience. An integrated system with 3D imaging, tool tracking, tool trajectory prediction and interactive user guidance would be highly beneficial.

Other current image-guided procedures such as CT-guided interventions, MRI-guided interventions, fluoro-based needle placements, or intraoperative CBCT-guided interventions require repeated acquisition of images associated with high radiation exposure, patient stress, suboptimal ergonomics or workflows, and/or cost. For percutaneous interventions requiring tool guidance, prediction of the tool trajectory is regularly based on repeated intraoperative imaging with the tools in place and "dead reckoning" on the part of the operator in how to re-position the tools to achieve satisfactory placement. Alternatively, the tool trajectory can be computed based on tracking sensors attached to the distal (external) tool end and system-supported display of extrapolated paths. However, this approach requires the previously discussed cumbersome registration.

The contributions of the current invention center on improvements to the workflow of image-guided interventions—specifically relating to simple and optimal application of markers for establishing and maintaining registration with secondary image data; real-time acquisition and reconstruction of said markers and patient surfaces; automatic registration methods utilizing said markers and surfaces; minimal-interaction methods allowing the operator to initialize said registrations; tracking methods for imaging probes, tools, patients, and displays; and methods for the estimation of deformations induced by the tracked objects.

The proposed invention may integrate real-time optical sensing, by camera modules with one or more cameras, into image-guided intervention systems. The functionality of these camera modules includes acquisition and tracking of markers and other surface features, interventional tools, and/or displays. For all of these types of tracked objects, real-time pose information may be extracted by an image processing unit and may be used for the generation of enhanced images by combining information from the real-time imaging data (which may include one or more imaging modalities other than optical sensing, such as ultrasound, SPECT, or others) with information from corresponding secondary image data based on the location of the camera modules in some embodiments of the current invention. Cameras may comprise combinations of one or more of: optical cameras, infrared cameras, UV-sensitive cameras, light field sensors, plenoptic cameras, or catadioptric cameras.

The image processing unit may process all incoming image data, whether secondary or real-time, by communicating with the real-time imaging sensors and by receiving secondary data. Tracking-relevant information may be extracted by segmentation from these inputs, whether this includes one or more markers, pre-existing features, or surface structures. Real-time imaging data may also be used by the unit to track interventional tools. In some embodiments of the current invention, the unit may be further responsible for registration between the input image data sets, and for computing enhanced images from the resulting combinations of image data sets and tracking information. Some of the image processing functions, such as computations, storage, or communications, may be performed by separate systems depending on the embodiment of the current invention, whether they are connected wired or wirelessly to the unit, are communicating through a local-area network, or are distributed throughout a network (for example, as remote servers or as "cloud services"). Conversely, such functions may also be integrated in an all-in-one computer or a tablet form factor.

Cameras may serve as the main input modality to enable tracking, observing tools and the patient (together called "objects" in this section) directly. However, unmodified objects may not exhibit sufficient features to allow successful initial registration and accurate continuous tracking, especially without additional assumptions about e.g. surface curvature or natural texture, external lighting, occlusion prevention etc. To ensure correct system operation under these circumstances, additional markers may be introduced into the environment. Depending on the embodiment of the current invention, these markers may include one or more of the following types: stick-on markers with self-identifying features (e.g., bar codes, QR codes, or April tags), multi-modality tags (visible in first imaging modalities such as optical cameras, and visible in second imaging modalities such as CT, MRI, fluoro, PET/SPECT etc.), markers in the shape of patterned flexible or rigid tapes that can be stuck to objects and provide mainly linear and limited perpendicular localization capabilities, patterned sheets (such as drapes and covers), patterned clothing (such as tight-fitting underwear shirts or similar with markings applied to the fabric), or natural features such as visible anatomical landmarks, skin texture, and/or hair.

Visual markers used for tracking may be both artificial markers as described before, and natural features such as hair, skin marks, anatomical features, and similar. To allow for continuous tracking around areas of interest, markers may be arranged so as to be visible from a multitude of different directions. In some embodiments of the current invention, these may then be collected by the guidance system successively, reconstructing their relative positions by localizing the camera module relative to known markers and simultaneously extending the geometry to newly-detected markers. To minimize reconstruction error along extended such collections, an iterative optimization procedure may detect loops in the resulting marker-relation graph, calculate the inherent error around these loops, and improve relative position estimates similar to "loop closing" in SLAM (Simultaneous Localization And Mapping) approaches to generate a well-conditioned visual marker mesh.

Markers may also be included in secondary image data sets. Although not required for automatic registration, these markers may be extracted automatically as well. With the strong priors of known marker geometry (shape) and marker location (on the surface of the patient), the image data may be analyzed to search for marker placement and orientation. Markers may be self-identifying by contained information that is discernible in the secondary image modality e.g. as variations in one or more of shape, radiopacity, radiation emissions, acoustic absorption, acoustic reflectivity, or magnetic resonance response. For self-identifying markers that also contain corresponding visual identifying encoding, observations in both visual data and in secondary image data sets may be associated to establish an unambiguous registration. Without such explicit associations, some embodiments of the current invention may automatically compute correspondences e.g. by repeatedly randomly selecting secondary marker tuples in RANSAC fashion and geometrically matching these to combinations of visual markers (or vice versa), or—because of the relatively small number of possible markers—by exhaustively trying all brute-force combinations.

In situations where no markers are present in secondary image data, a registration initialization may be provided to improve registration for some embodiments of the current invention. In these cases, an "anchor marker" (that allows for marker orientation recovery) may be used, for which the system may heuristically propose a placement to the operator and expect the anchor marker's actual location on the patient as later placed by the operator to closely correspond to the proposed one to initialize subsequent registration refinement steps. The operator may be allowed to modify the proposed placement of the anchor marker to better match intraoperative requirements, such as visibility constraints or prior knowledge about suitable locations that are representative of the position of the patient's relevant anatomy, such as locations close to rigid bone structures.

Figure 9:
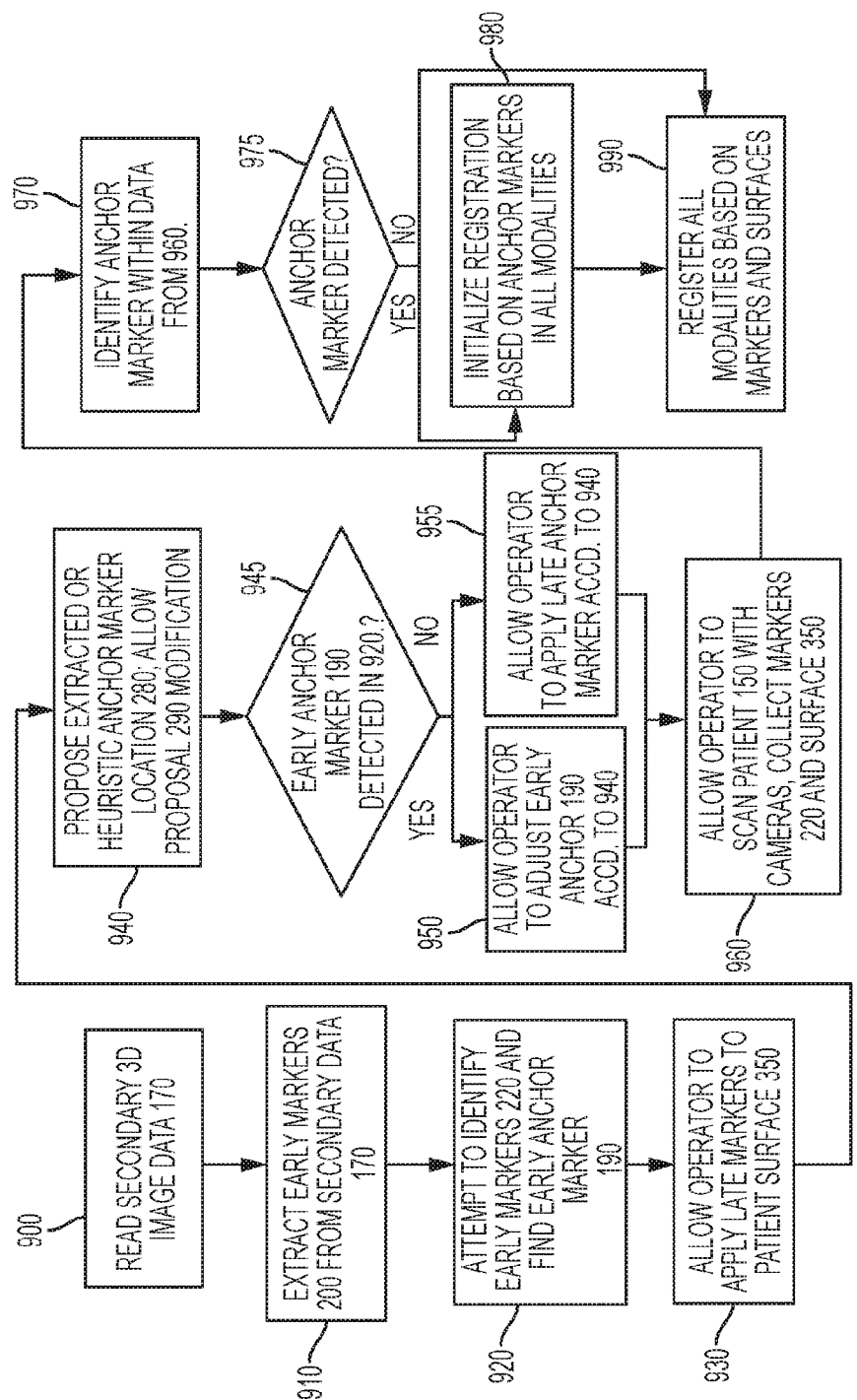
FIG. 9 depicts a sample registration workflow according to an embodiment of the current invention.

Depending on the availability of different tracking-relevant data, embodiments of the current invention may use variations of a common sequential registration approach. FIG. 9 depicts a sample registration workflow according to an embodiment of the current invention showing optional steps to the basic function of the approach. In 900, secondary 3D image data 170 may be read. From 900, flow may move to 910.

In 910, early-attached markers (or "early markers") 200 may be extracted from secondary data 170. From 910, flow may move to 920.

In 920, early markers 220 may be identified and early anchor marker 190 may also be found or detected from the secondary data 170. From 920, flow may move to 930.

In 930, an operator may apply "late-attached markers" ("or late markers") to a patient surface (e.g., skin, clothing, bandages, etc.). The late markers may be clustered around a region of interest. From 930, flow may move to 940.

In 940, an anchor marker location may be determined and proposed to the operator. The proposed anchor marker location may be heuristically computed and/or detected from the secondary data. The proposed anchor marker location may allow for manual modification of the proposed anchor marker location. From 940, flow may move to 945.

In 945, if an early anchor marker was detected, then flow moves to 950, if an early anchor marker was not detected, flow moves to 955.

In 950, an operator may adjust the early anchor marker to, for example, better match the previously proposed position. From 950, flow may move to 960.

In 955, an operator may apply a late anchor marker to the patient surface near or at, for example, the previously proposed position. From 955, flow may move to 960.

In 960, the patient 150 may be visually scanned with cameras 100. The system may collect a well-conditioned visual marker mesh from one or more of early markers, late markers, anchor markers, or natural features. The system may reconstruct a patient surface from these observations. From 960, flow may move to 970.

In 970, the anchor marker may be identified using the data collected in 960. From 970, flow may move to 975.

In 975, if an anchor marker was detected, flow moves to 980. If an anchor marker is not detected, flow moves to 990.

In 980, registration may be initialized based on anchor markers in all modalities. For example, the patient surface and the secondary image data may be initially (coarsely) registered by aligning anchor markers in all modalities. From 980, flow may move to 990.

In 990, all modalities may be registered based on markers and surfaces. For example, possibly starting from a coarse initial registration, the patient surface and the secondary image data may be finely registered using one or more of markers or surfaces.

Registration may be started directly after a marker position is visually established for some embodiments of the current invention. This may still allow for continuing collection and integration of further visual markers into the observed marker mesh, while providing an intuitive—if less precise—registration behavior while marker collection is ongoing.

Camera location may be calculated in at least two different ways depending on embodiments of the current invention—by localizing markers in camera coordinates (and thus localizing the camera relative to the observed marker set), and/or by collecting an observed marker mesh and registering it to the secondary image data (and thus localizing the camera relative to said image data). For cameras mounted on a secondary imaging device or display, this may allow localization of said device or display relative to the markers or registered secondary image data as well.

The cameras may serve to track tools as well in some embodiments of the current invention. Using real-time observations of the environment, tools with known geometries (such as needles) and/or carrying known markers may be tracked relative to the camera, from where coordinates may be transformed into handheld imaging, display, and/or secondary image data coordinates. Tools with known geometries or patterns may be tracked including their respective tool tips and/or points of interest.

The image processing unit may then display the enhanced images computed from registered data on a display, which may be directly connected to the unit, or be portable, or be a smart display that is wirelessly connected to the unit or that contains the unit itself or that contains components that communicate with image processing components connected through a network, depending on the embodiment of the current invention. Some variations of such enhanced images may include digitally reconstructed radiographs (DRR), multi-plane or variable-plane reconstructions (MPR/VPR), registered augmented-reality overlays (AR) of information from secondary data and/or real-time imaging, overlays of targets registered onto different image types, registered fused images, and overlays of tracked tools onto different image types.

Cameras may be included in handheld displays to allow for real-time imaging and/or tracking of patient and/or tools directly from the display's point of view for some embodiments of the current invention; cameras may also be positioned externally to the display and possible secondary imaging devices and track displays and/or imaging devices and/or tools from a distinct position for some embodiments of the current invention.

The real-time imaging module including the one or more cameras may also comprise secondary imaging sensors such as US, handheld SPECT probes, oximeter sensors etc. in some embodiments of the current invention. These may be physically coupled to the cameras (to ensure a rigid registration relationship and more precise tracking) or separate (to allow for greater manipulability and compactness).

Targets may be defined in secondary image data, or interactively by the operator into secondary data or real-time imaging data. For some embodiments of the current invention, this may be achieved in 2D e.g. by inputs directly onto a displayed image (such as tapping or clicking onto an ultrasound view or onto a planar view from a volumetric data set), or in 3D data e.g. via epipolar definition through a 2D point from one view direction, which may then be redisplayed as a 3D line from another view direction and refined by defining another point on or close to that line. Targets may be automatically segmented from both kinds of imaging data if they are distinct from the environment or their location can be inferred from any combination of the input image modalities.

In some embodiments of the current invention, the cameras may observe patient surface deformations relative to secondary data (such deformations can be observed on the surface e.g. via structured light, shape-from-shading, time-of-flight, or directly from stereo, or can be inferred from observed marker movements). The surface deformation estimation may be performed or improved relative to observations by modeling collisions with a known handheld imaging probe or tracked tools or other objects with known geometries and location. The image processing unit may then compute a resulting initial deformation of secondary data by propagating the observed or inferred deformation to the surface of the secondary image data. If the patient surface is then further deformed relative to an initial configuration, the image processing unit may then similarly compute resulting real-time deformations of the secondary data. Furthermore, the surface deformation may be propagated into the tissue represented in secondary or real-time imaging, e.g. according to a finite-element model (FEM) or a spring-mass model derived from said imaging data. Using the resulting tissue deformation, an updated resulting translation of defined targets may be computed.

Some embodiments of the current invention may then compute enhanced deformed images in real time according to the resulting deformation of the input image data, and display the resulting deformed images, possibly together with updated target positions.

Some embodiments of the current invention may include with the real-time imaging unit, mobile displays, and/or tools one or more sensing devices with one or more of inertial measurement units (IMU, such as accelerometers or gyroscopes) or magnetometers to provide ongoing orientation and translation estimates to allow for "dead reckoning" tracking to facilitate calculation of updated tracking, deformation, and/or enhanced images.

If real-time imaging shows a poor marker configuration (such as collinear tag arrangements; insufficient density of markers around regions of interest such as anchor marker, intervention area, patient surface areas with distinct curvature, target locations etc.; inaccurate placement of the anchor marker), some embodiments of the current invention may have the image processing unit compute and propose an improved configuration to the operator.

FIG. 1 shows an embodiment of an imaging system according to an embodiment of the current invention. Handheld unit 160 includes one or more cameras 100, display 230, and image processing unit 110. Handheld unit 160 may be, for example, a tablet, a notebook, or smartphone, and one or more cameras 100 and image processing unit 110 may be internal components of handheld unit 160. However, the broad concepts of the current invention are not limited to only this example. In the example of FIG. 1, the one or more cameras 100 observe a patient 150 or sections of said patient within one or more viewing cones 120 of the one or more cameras 100. Within a viewing cone, there may be one or more markers 220 or interventional tools 130. The markers 220 can be of one or more of the following kinds, and may be attached to the patient or be previously present: self-identifying visual markers 630, multi-modality markers 640, marker strips 650, or visually distinguishable natural features such as hair, birthmarks, or anatomical features. In certain situations, a geometric transformation 140 between cameras and environment can be determined from input data including, for example, data received from the one or more cameras 100.

FIG. 1 also illustrates different embodiments of the current invention where the image processing unit 110 is coupled with handheld unit 160, or where the image processing unit 110 comprises or communicates with additional remote components that are connected through a network, or where some functions of the image processing unit 110 are performed remotely in the "cloud".

A secondary 3D image data set 170 of the patient 150 may be collected and may include pre-defined targets 180 and/or representations of early markers, possibly including representations of early anchor markers 190 (an anchor marker is a specific marker that allows extraction of orientation information). Such secondary image data 170 may be transferred into the image processing unit for further processing and/or display on, for example, display 230.

Depending on the embodiment of the current invention, image processing units 110 may include one or more integrated circuits and/or microprocessors. The image processing unit 110 may execute instructions for tracking markers, needles, and/or surgical tools (e.g., interventional tools 130). The image processing unit 110 may receive a target selection 180 (e.g., a tumor, a vessel, a suspicious lesion, or other clinically relevant sites) in the secondary 3D images 170, or a new target selection directly in the images from the one or more cameras 100. The new target selection may be received from a touchscreen display 230 displaying the images, for example. The image processing unit 110 may also track the tool; display a representation of the tool in the display 230 as the tool is being tracked; indicate a tool tip in the display 230 (e.g., though the use of one or more perpendicular lines, pointed line arrangements, and/or color variations); calculate a distance between the tool tip and the target; output audio, wherein the audio changes based on the calculated distance between the tool tip and the target; display the calculated distance between the tool tip and the target; output visual cues as to the quality of the tool tracking; and/or indicate a loss of tool tracking though audio or visual cues. The image processing unit 110 may further instruct the display 230 to display the tracked tool as a line or further to represent the quality of the tool tracking as a function of the observed length of the tracked tool. For the specific example of a tracked tool 130 intersecting an observation region of cameras 100, there will be a certain segment of tool 130 physically contained within the region. The orientation of this segment relative to defined targets can be computed by the image processing unit 110 based on the tracking and registration information between cameras 100, tool 130, and/or secondary 3D image data 170, and be used as an input for tool tracking.

Figure 2:
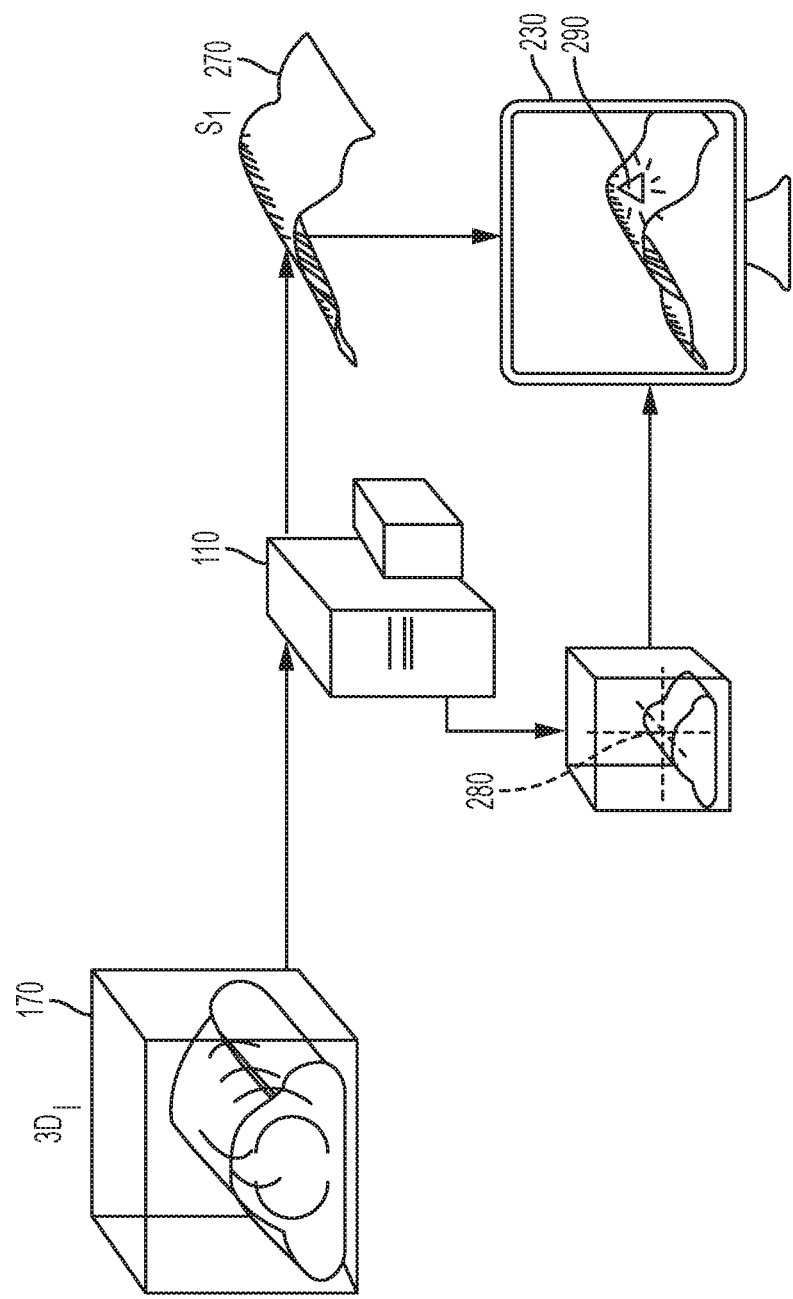
FIG. 2 shows another embodiment of an imaging system performing functions according to an embodiment of the current invention.

FIG. 2 depicts an embodiment of an imaging system according to an embodiment of the current invention, describing a step of an image-guided procedure according to an embodiment of the current invention. From secondary 3D image data 170, an image processing unit 110 may extract a patient surface 270. Within said secondary 3D image data 170, said image processing unit 110 may compute a proposed late anchor marker location 280. Secondary 3D image data 170 or patient surface 270 may then be displayed together with a representation 290 of the late marker location on a display 230.

Figure 3:
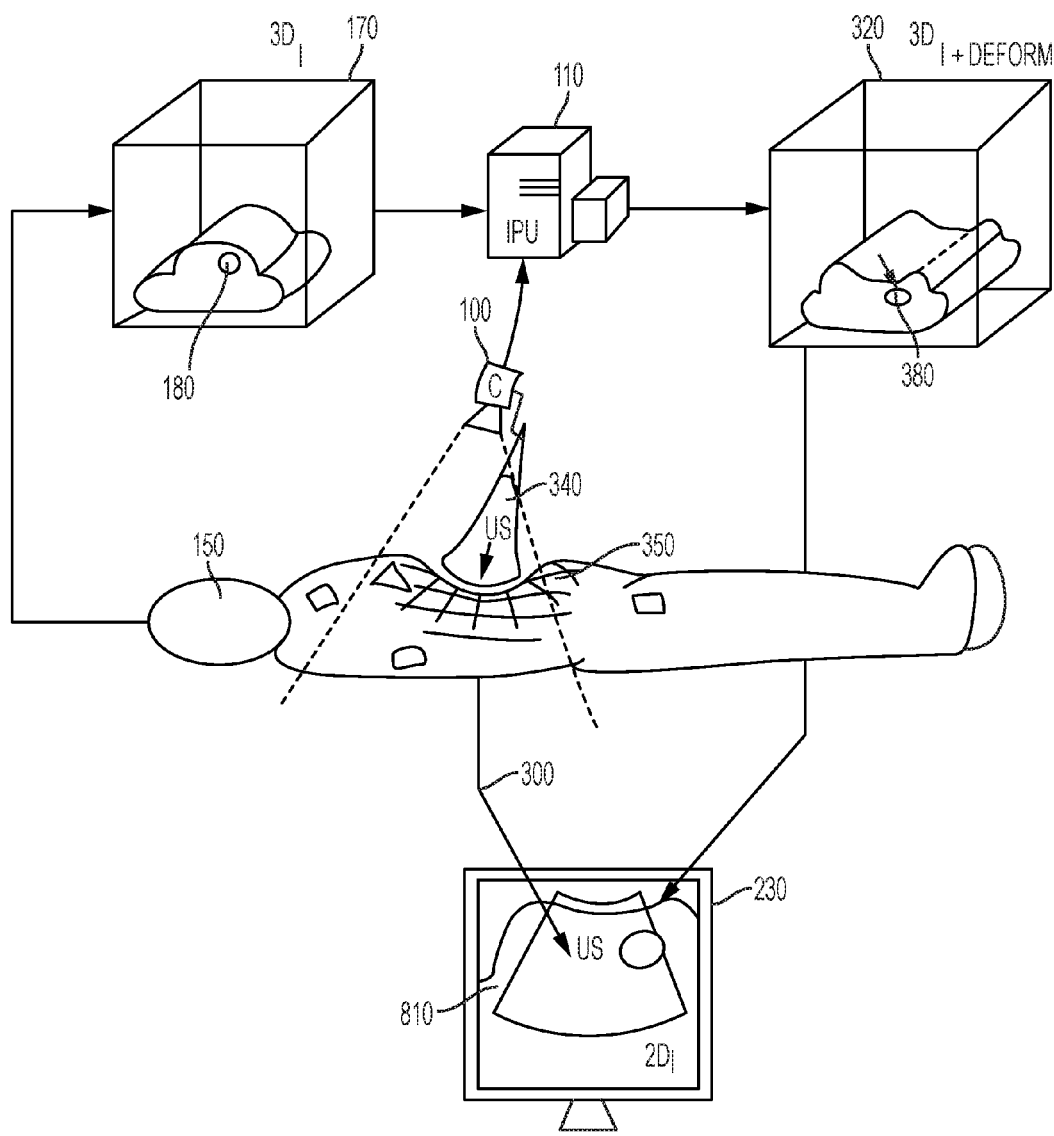
FIG. 3 shows another embodiment of an imaging system according to an embodiment of the current invention.

FIG. 3 depicts an embodiment of an imaging system according to an embodiment of the current invention, describing a step of an image-guided procedure according to an embodiment of the current invention. From secondary image data 170 and observations through one or more cameras 100 of a deformation of a patient's 150 surface 350 effected by an interventional instrument and/or imaging device 340, an image processing unit 110 may compute a deformed variation 320 of secondary image data 170, e.g. by imposing the surface deformation as an initial boundary condition onto e.g. a mass-spring model or a finite element model that was heuristically derived from the secondary 3D image data 170, e.g. by regular meshing of a binary-thresholded secondary 3D image data set 170 followed by parameterization of model parameters according to voxel intensities from said image data set. From the deformed variation 320 of secondary image data 170, said image processing unit 110 may compute transformations 380 of pre-defined targets 180. Said deformed image data 320 may then be displayed together with said targets 380 on a display 230.

Figure 4:
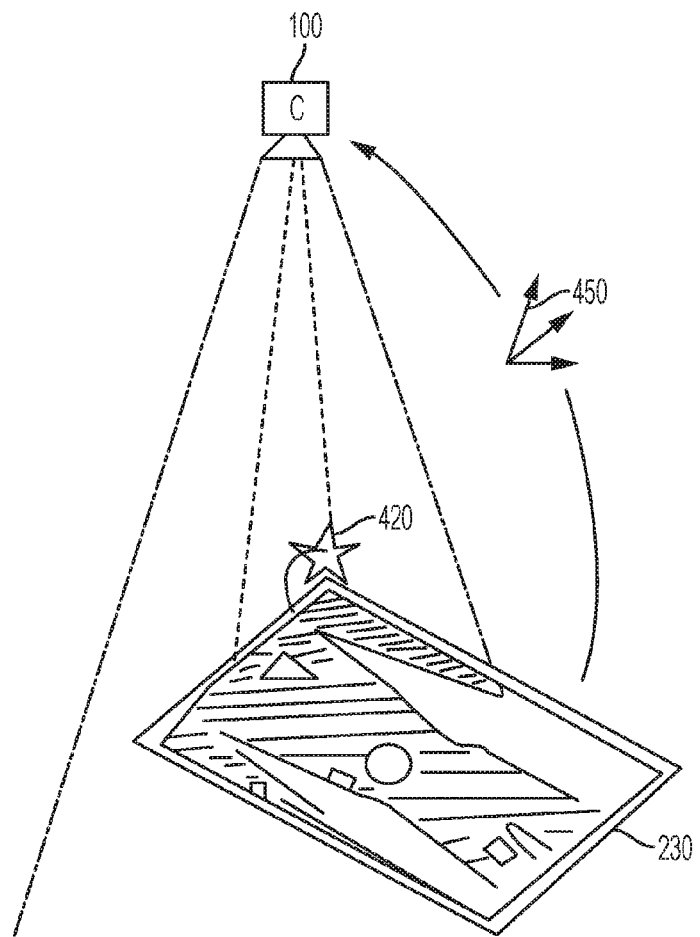
FIG. 4 shows another embodiment of an imaging system according to an embodiment of the current invention.
Figure 4:

FIG. 4 shows an embodiment of a guidance system according to an embodiment of the current invention. An external camera 100 may observe a patient 150 with attached markers 220, as well as a display 230, possibly with attached markers 420. Observations of surfaces and markers can be geometrically matched with prior knowledge about or observations of same, e.g. by using the well-known Arun or Horn registration methods (when using self-identifying markers with correspondences), a RANSAC variation (without self-identifying markers or with unknown correspondences), or ICP registration (without correspondences) for sets of markers or for surfaces, or e.g. visual fiducial tracking for single markers (E. Olson: "A robust and flexible visual fiducial system", IEEE ICRA 2011). This geometrical match is a registration transform between a reference pose and the current observation pose. Based on such a registration transform 450 of the display relative to the patient (the combination of the display-to-camera and the inverse patient-to-camera transforms), an image processing unit 110 may compute enhanced images that include information depending on the pose of the display 230.

Figure 5:
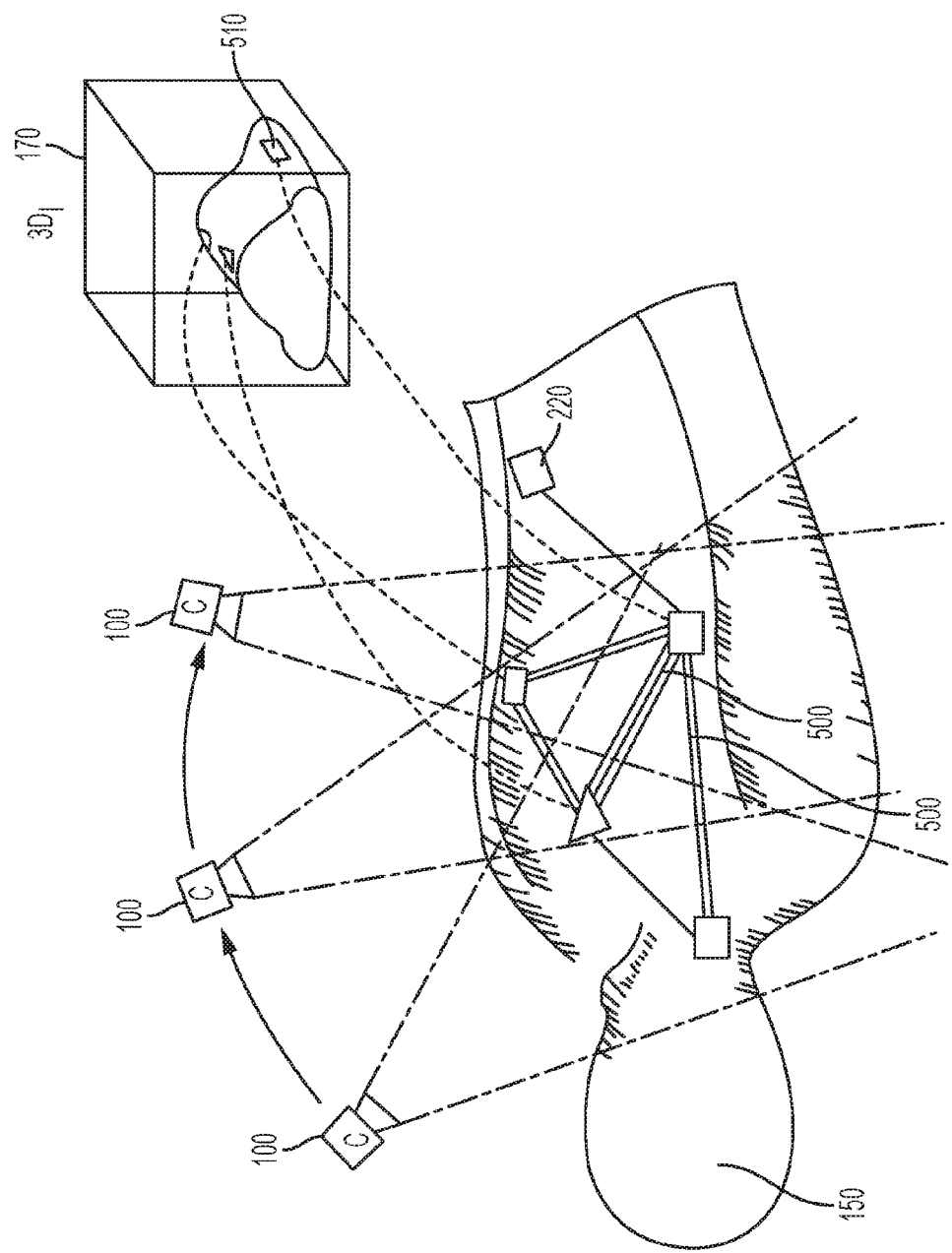
FIG. 5 shows another embodiment of an imaging system performing functions according to an embodiment of the current invention.

FIG. 5 depicts aspects of an embodiment of an imaging system according to an embodiment of the current invention, describing a step of an image-guided procedure according to an embodiment of the current invention. While one or more cameras 100 may be moving through one or more poses relative to the patient 150, different subsets of patient surface markers 220 may be observed. The image processing unit 110 may determine the marker poses relative to each other, e.g. from pairwise observations, and successively reconstruct a partial or complete marker position graph 500. In some embodiments of the current invention, this marker set underlying the graph 500 may later be used for one or more of visual tracking, registration to secondary 3D image data 170 using "early markers" 510 from secondary image data, and/or registration to secondary data 170 using surfaces 270 generated from said data, as described in the preceding paragraph.

Figure 6:
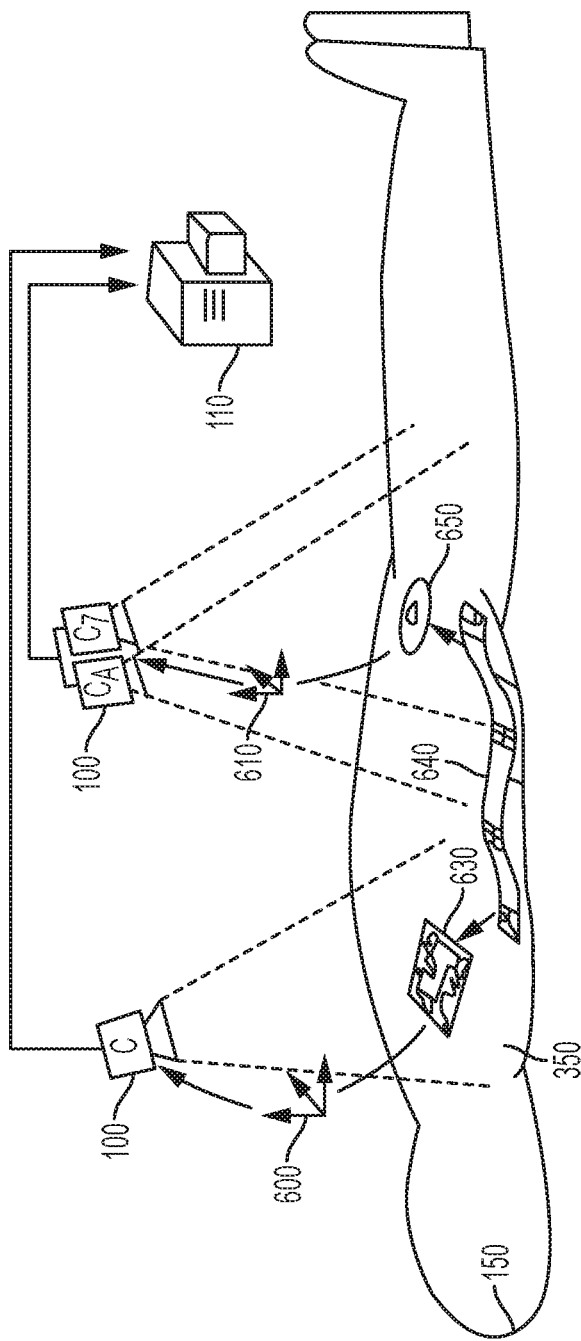
FIG. 6 shows embodiments of a marker component for an imaging system, and shows imaging components performing functions according to an embodiment of the current invention.

FIG. 6 illustrates aspects of variations between different embodiments of the current invention. The image processing unit 110 may be connected to modules of one or more cameras 100. Each of these cameras may be configured to observe a patient 150. On the surface 350 of said patient, one or more of the following kinds of markers or features may be attached, combined on a patterned sheet or on patterned clothing, or previously present: self-identifying visual markers 630, multi-modality markers 640, marker strips 650, or visually distinguishable natural features such as natural anatomical features, skin features, or hair.

Figure 7:
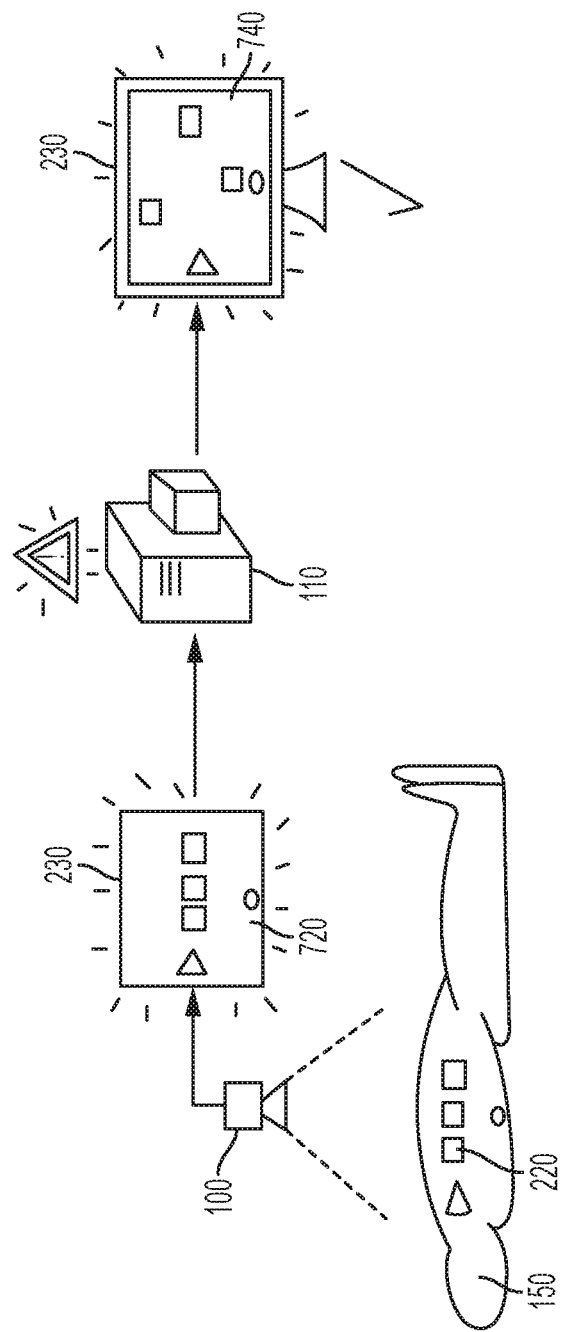
FIG. 7 shows another embodiment of an imaging system performing functions according to an embodiment of the current invention.

FIG. 7 depicts an example workflow describing a step of an image-guided procedure according to an embodiment of the current invention. One or more cameras 100 connected to an image processing unit 110 may be configured such that they may simultaneously or successively observe a plurality of patient markers 220 on a patient 150. The image processing unit 110 may be configured such that it detects non-optimal configurations of markers, such as e.g. collinear arrangements 720, and that it displays a proposed improved configuration 740 on a connected display 230.

Figure 8:
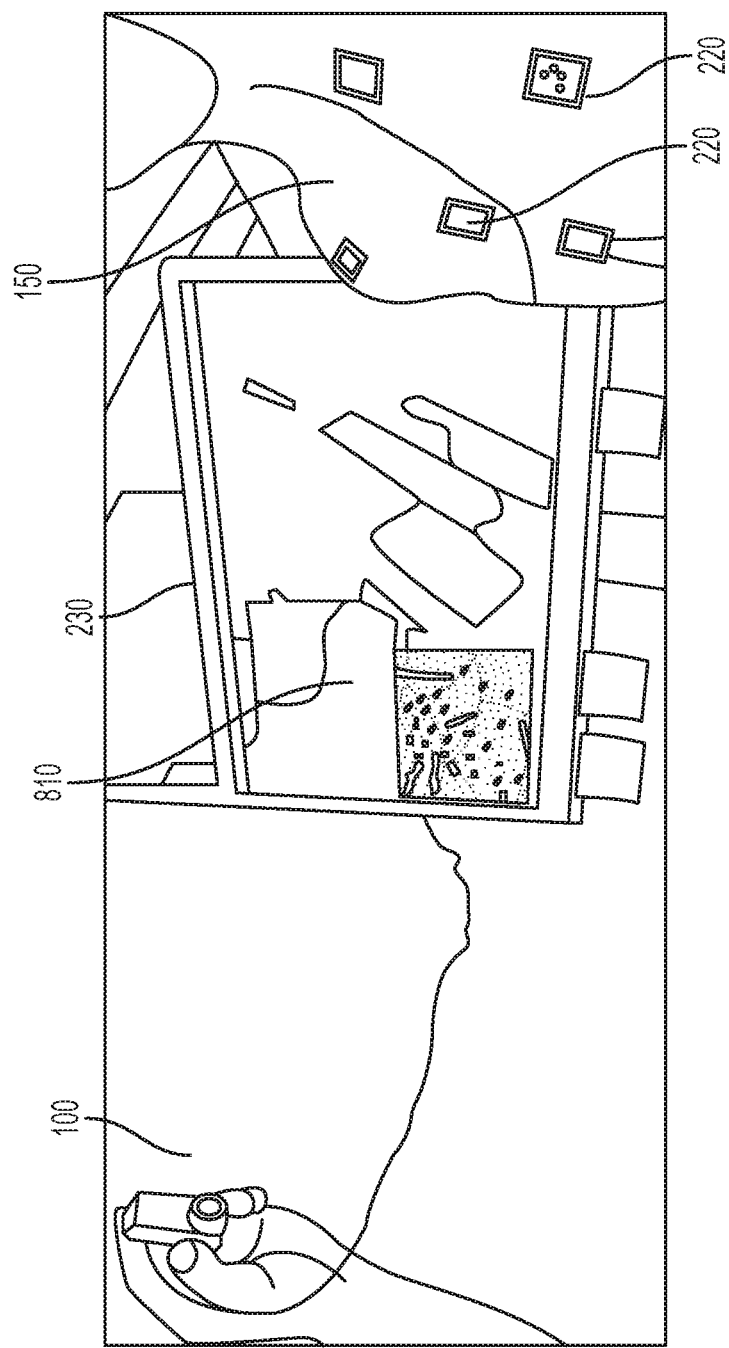
FIG. 8 shows another embodiment of an imaging system performing functions according to an embodiment of the current invention.

FIG. 8 shows an embodiment of a guidance system according to an embodiment of the current invention. An external camera 100 may observe a patient 150 with attached markers 220. Based on the tracked pose 450 of the camera relative to the patient, an image processing unit 110 may compute enhanced images 810 that include information depending on the pose of the camera, and display these images on a connected display 230.

In an embodiment, tracking of a tool 130 (e.g. needle or surgical instrument) may be accomplished through one or more visible features on the tool. (Basic tool tracking has been described in previous publications by the inventors, such as Stolka et al. "Navigation with local sensors in handheld 3D ultrasound: initial in-vivo experience.", SPIE Medical Imaging 2011, Lake Buena Vista, Fla./USA, pp. 79681J-79681J. International Society for Optics and Photonics, 2011; Wang et al. "The Kinect as an interventional tracking system;" SPIE Medical Imaging, San Diego, Calif., USA, pp. 83160U-83160U. International Society for Optics and Photonics, 2012; Hager and Toyama "The XVision System: A General-Purpose Substrate for Portable Real-Time Vision Applications", in Computer Vision and Image Understanding 69(1) pp. 23-37, all of which are included by reference in their entirety.) The visible feature may include a detectable pattern, the pattern being initially created using a pseudo random binary sequence, or more generally a de Bruijn sequence, wherein the pattern is one of marked, printed, etched, or applied to the tool (Stolka et al., "Surgical needle for a surgical system with optical recognition", U.S. Pat. No. 8,880,151 B1). The pattern may be used to detect insertion depth of the tool into a human or animal body. Alternatively, the visible feature may include an attachment such as a ring attached to the tool. The ring may be reflective and/or cylindrical or handle shaped. The ring may include a detectable pattern used in calculating an insertion depth of the tip of the tool, the detectable pattern may be initially created using a pseudo random binary sequence. Imaging system 110 may initially calculate a distance from the ring to the tip of the tool and use this calculated distance to calibrate the imaging system for tool tracking.

Example System 1 ("Moonlight")

One persistent challenge in image-based medicine is the use of secondary 3D image data 170 that is acquired without explicit provisions for registration to an interventional situation. Some examples for this may be pre-existing volumetric CT, MRI, PET, SPECT, or CBCT scans, but also 2D image data such as fluoroscopic or generally x-ray projections that are acquired in close spatial and temporal proximity to an interventional situation. Any of these secondary image data sets may or may not include markers that could be used for registration, e.g. well-known standard multi-modality stick-on markers that feature a small radiopaque sphere on a colored disk. For such secondary image data sets, alignment of relevant image parts with the actual patient situation is difficult and time-consuming. Often, the operator has to mentally reconstruct the correct anatomical matches, and remember important features throughout the intervention.

With an image processing unit 110, it is possible to compute enhanced images from such secondary image data sets 170 that highlight or correspond to certain aspects of an interventional situation, such as the relative orientation of anatomical features, when observed from certain viewing directions. The secondary image data sets 170 may be imported into the image processing unit 110 through combinations of one of more or storage media, communications networks, or connections to imaging devices. The image processing unit 110 may then communicate with a display 230 which shows the enhanced images 810.

Using one or more cameras 100 or other light-sensitive devices, the interventional environment may be observed, possibly including views of the patient 150 or interventional tools 130, either of which may be adorned with attached markers 220 or other visible features 220 that remain stationary relative to their respective objects. Based on these observations of objects or features, the position of the cameras 450 may be tracked in an object or feature coordinate system as measured from a reference position.

If such one or more cameras 110 or other light-sensitive devices are attached to a handheld display 230 or integrated handheld unit 160, the images they capture may serve as inputs to programming of the image processing unit 110 to effectively determine the position of the display in space relative to the patient 150. This position may then be interpreted as the afore-mentioned viewing direction for computation of enhanced images from the secondary image data sets 170. Furthermore, such one or more cameras 110 or other light-sensitive devices may then be used to capture views of tools 130 or other objects the position of which is desirable to be known relative to the patient. These views may then also be processed by an image processing unit 110 to determine said tool positions. Finally, these tool positions may be used to provide overlaid guidance information on the enhanced images, e.g. by drawing one or more of lines, boxes, cylinders, dots, or circles that correspond to 2D projections of the tool positions onto the enhanced images, indicating the relative poses of the tools and the secondary image data sets.

One example embodiment of the current invention ("Moonlight") implementing some of the described aspects may work as follows. Properties of such a system are described herein, although they may be accompanied by various combinations of other properties without affecting the principle of operation. A handheld computer 160 such as a tablet, notebook, or smartphone includes a display 230, a central processing unit 110 performing image processing unit functions (an "image processing unit"), a camera module (including one or more cameras, mounted to the display or physically separate) 100, storage, and data connections. The general functionality of this embodiment is navigation through a 3D image data set 170 using a handheld camera 100, with the image processing unit 110 computing enhanced images 810 from the 3D image data set 170 in real time and from the point of view of the handheld camera 100, and with the display 230 being either integrated with the handheld camera 100 or connected to that camera 100 and displaying the enhanced images 810. The position of the handheld camera 100 relative to an environment (such as a patient 150 or a workpiece) which is represented in the 3D image data set 170 is computed based on observations of that environment. A transformation 450 (also referred to as a registration) between the camera 100 and the environment is computed by the image processing unit 110 based on one or more of observed and computed surface information 270, markers 220, or natural or anatomical landmarks. Optionally, interventional tools 130 may be actively tracked by observing them with the camera 100 and detecting them by the image processing unit 110. The image processing unit 110 is programmed in such a way as to enable the necessary computations to achieve the described functionality, with more detail following. Certain steps of operation need not be executed in the order described.

Figure 10:
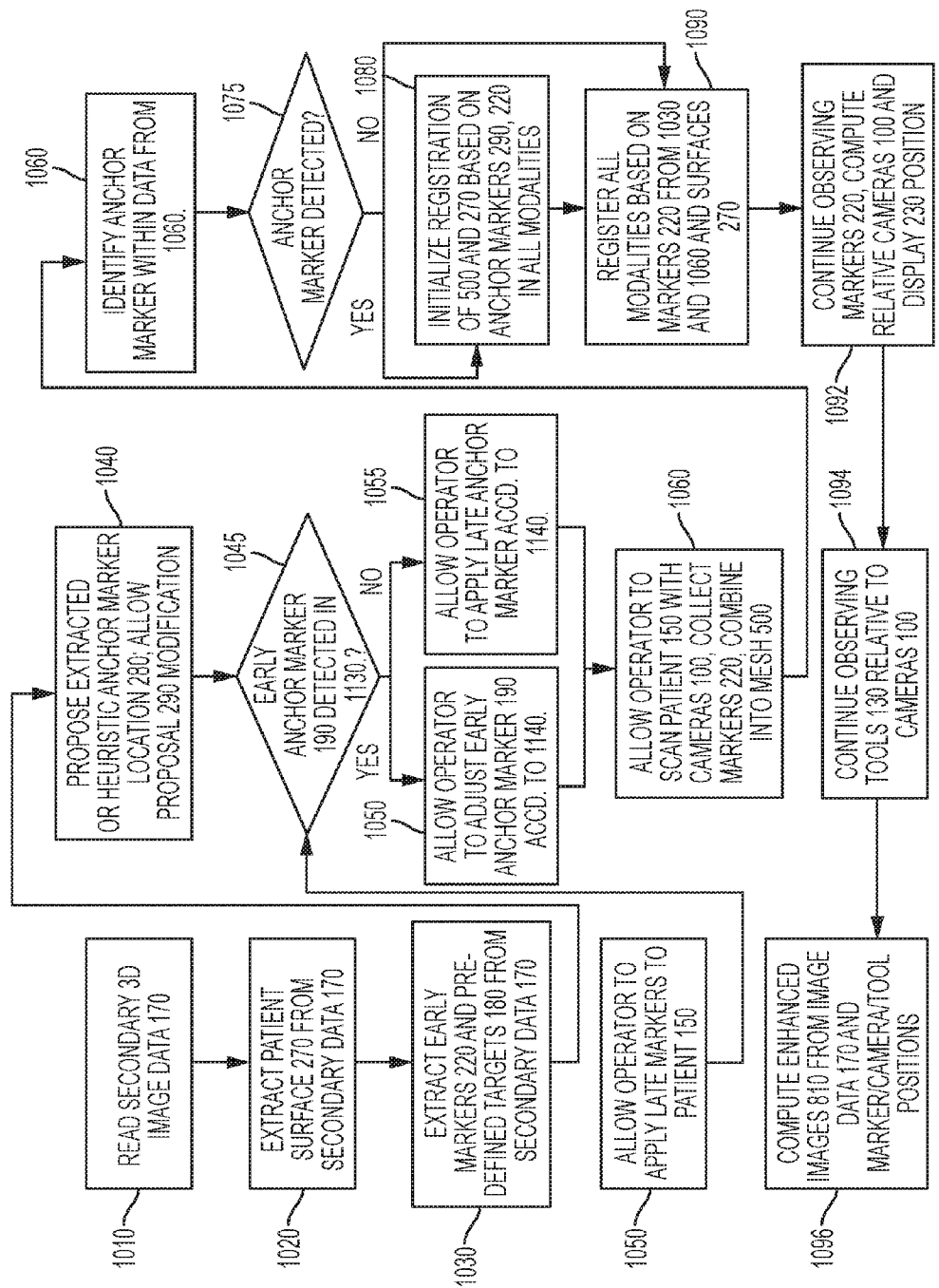
FIG. 10 depicts a sample workflow according to an embodiment of the current invention.

FIG. 10 depicts a sample workflow according to an embodiment of the current invention. In 1010, secondary 3D image data set 170 (e.g., CT or MRI) may be read by the image processing unit 110 from a storage medium or other communication partner. From 1010, flow may move to 1020.

In 1020, the secondary 3D image data set 170 may be processed to extract a patient surface 270. From 1020, flow may move to 1030.

In 1030, the secondary 3D image data set 170 may be processed to extract potentially included markers 220 or other surface features, as well as potentially pre-defined targets 180. All four data elements (volume 170, surface 270, markers 220, and targets 180) may be retained for further processing, if present. From 1030, flow may move to 1040.

In 1040, to allow for correct registration initialization, image processing unit 110 may compute a proposed anchor marker position 280 for, and may permit setting a virtual position for, an on-screen "anchor marker" 290 that roughly defines later orientation and position of a corresponding surface location on the patient 150. This anchor marker position may be extracted from the 3D image data set (if present as an "early marker") or initialized heuristically (e.g. "on the top center of the patient") for later attachment to the patient by the operator (as a "late marker"), approximately according to the defined on-screen position. From 1040, flow may move to 1045.

In 1045, if an early anchor marker 190 is detected, flow moves to 1050, if not, flow moves to 1055.

In 1050, the operator may adjust early anchor marker 190 according to 1040. From 1050, flow may move to 1060.

In 1055, the operator may apply a late anchor marker according to 1040. From 1050, flow may move to 1060.

In 1060, operator may scan patient 150 with cameras 100. Markers 220 may be collected and combined into mesh 500. From 1060, flow may move to 1070.

In 1070, the anchor marker may be identified from data collected in 1060. From 1070, flow may move to 1075.

In 1075, if an anchor marker is detected, flow moves to 1080, if not, flow moves to 1090.

In 1080, registration of mesh 500 and patient surface 270 may by initialized based on anchor markers in all modalities. From 1080, flow may move to 1090.

In 1090, all modalities may be registered based on markers 220 from 1030 and 1060 and surfaces 270. From 1090, flow may move to 1092.

In 1092, markers 220 may continue to be observed, and relative position of cameras 100 and display 230 may be computed. From 1092, flow may move to 1094.

In 1094, tools 130 relative to cameras 100 may continue to be observed. From 1094, flow may move to 1096.

In 1096, enhanced images 810 from image data 170 and marker/camera/tool positions may be computed.

Independent of the processing subsequence of the preceding paragraph, a second subsequence acquires real-time situational information through the one or more cameras 100. Initially, the operator is allowed to attach additional late markers 220 to the patient 150, including (but not requiring) an actual anchor marker, whose orientation and position on the patient 150 should approximately match the on-screen anchor marker's 290 orientation and position on the secondary 3D image data's 170 surface 270. The operator-initiated late marker attachment is not required, but provides a larger number of more clearly detectable features for later tracking, particularly if no early markers were present in the secondary 3D image data 170. The one or more cameras 100 are moved around and observe the environment and acquire real-time images for further processing by the image processing unit 110. The image processing unit 110 continuously analyzes the real-time images to detect markers 220 or other features on the surface of the patient 150. The image processing unit 110 combines these observed markers 220 or features into an optimal observed marker mesh 500 containing their relative poses. Depending on the presence of markers or features extracted from the secondary 3D image data set 170, this marker mesh 500 is registered by the image processing unit 110 to one or more of the patient surface 270 or the extracted markers 220 or features, and therefore to the secondary 3D image data set 170. This registration is initialized by matching the on-screen anchor marker 290 with the observed actual anchor marker 220, if an anchor marker is used; otherwise no initialization is performed. If corresponding early markers 220 are present in both the 3D image data set 170 and the observed marker mesh 500, the marker sets can be registered rigidly (e.g. by the method described in Arun et al. "Least-Squares Fitting of Two 3-D Point Sets", 1987 IEEE). Otherwise, an algorithm such as Iterative Closest Point (ICP; cf. Paul/McKay, "A Method for Registration of 3-D Shapes", IEEE 1992) can be used to find a local registration optimum using one or more of markers or surfaces. If such a local optimum is later determined by the operator to be inaccurate (e.g. based on the resulting overlay positions, as described below), the registration can be re-initialized by on-screen modification of the virtual anchor marker 290 or by re-positioning the actual anchor marker 220. Continuous marker or feature detection in the camera images by the image processing unit 110 localizes the one or more cameras 100 relative to the markers 220 or features, and thus to the marker mesh 500, and thus to the registered secondary 3D image data set 170. The image processing unit 110 may detect tools 130 and their poses in the acquired camera images (e.g. by following Stolka et al. "Navigation with local sensors in handheld 3D ultrasound: initial in-vivo experience", SPIE Medical Imaging 2011). The image processing unit 110 generates enhanced images 810 from the secondary 3D image data set 170 depending on one or more of the camera 100 location, the display 230 location, or tool 130 locations, which are known relative to the camera 100 location. These enhanced images 810 can for example take on the form of digitally reconstructed radiographs or single- or multi-plane reconstructions based on camera/display/tool positions, or other clinically relevant transforms. These enhanced images 810 can also include overlays of observed tool 130 and transformed target 180 positions. During this procedure, targets 180 may also be created interactively e.g. by tapping on the display 230 when held at different viewing positions, defining an epipolar geometry that identifies targets at ray intersection locations.

Such a system allows the navigation through secondary 3D image data sets 170 by means of positioning a handheld display 230 or camera 100, which together effectively serve as a "window" into the image data 170. Importantly, the registration of the patient 150 with the image data 170 is achieved by means of real-time acquisition of one or more of surfaces 270 and surface markers 220 or features, which are immediately registered onto the secondary 3D image data 170 (as described in the preceding paragraph) without requiring further operator interaction. Visual observation of surfaces and markers or features allows for both dynamic large-scale (long-range) registration as well as continuous small-scale (short-distance) tracking Tool 130 poses and transformed target 180 locations are overlaid directly onto the image data 170 on the display 230, allowing for effective tool positioning relative to sub-surface anatomical structures without lengthy manual initialization steps. Surface markers 220 or features may be present in and be used for patient 150 registration with secondary 3D image data 170, but crucially need not be present on the patient until the time of intervention.

Example System 2 ("Moonlander")

The operation principle of Example System 1 can be extended to include secondary medical real-time image data beyond camera images. This may serve to combine different medical imaging modalities with different resolutions or functional or material or temporal imaging characteristics. Examples of handheld secondary sensors would be ultrasound probes, SPECT probes, oximeters, optical vessel visualization devices, whereas examples of stationary secondary sensors would include C-arms, O-arms, fluoroscopes, or ultrasound tomographs. As such, another example embodiment of the current invention ("Moonlander") may incorporate real-time handheld ultrasound imaging. Properties of such a system are described herein, although they may be accompanied by various combinations of other properties without affecting the principle of operation. This system is based on Example System 1 ("Moonlight"), but additionally receives ultrasound image data 300 through direct connection or indirectly through another ultrasound system by means of imaging with a handheld probe 340, to which a stereo camera component 100 is rigidly attached and calibrated. Together, the handheld ultrasound probe 340 and stereo camera component 100 form a real-time imaging module. The system display 230 could but need not be a handheld display 160. By tracking the ultrasound probe position relative to a registered secondary 3D image data set, the system may compute enhanced images that combine real-time ultrasound imaging with geometrically appropriate information extracted from the secondary 3D image data set to display both modalities together in real time, thus helping the operator to discern image aspects that would be difficult to discover in a single modality. Knowledge about tracked ultrasound probe and tool positions relative to the registered secondary 3D image data set may further allow computing deformations of said image data, and to display geometrically adjusted information based on said deformations.

Whereas most operation characteristics and procedure steps are similar to those in Example System 1, the image processing unit 110 further may receive ultrasound image data 300. This data may be used in the computation of enhanced images 810, for example by overlaying it onto planar reconstructions or into 3D visualizations of the 3D image data sets 170.

With the position and the shape of the handheld probe 340 known (from tracking and modeling, respectively), collisions with the secondary 3D image data 170 or the surface 270 extracted from the latter may be detected indirectly, and the collision geometries may be computed (e.g. by computing the intersection of image data 170 with a model of probe 340, or by displacing elements of the surface 270 by the intrusion depth of probe 340 into image data 170 or surface 270). These collisions induce tissue deformations, whose propagation may be estimated by the image processing unit 110 by means of a mechanical deformation model that has been previously created based on the secondary 3D image data 170 and estimated tissue properties. Such estimations may be based e.g. on atlases or on intensity-based segmentations. Collisions may also be independently deduced from direct observations of surface deformations 350 or marker mesh deformations. Propagated deformations into the deformation model may then inform deformations 320 of the secondary 3D image data 170 or of enhanced images 810 derived from said data, possibly including deformations 380 of pre-defined targets 180. These image deformations and target displacements may then finally be displayed together with real-time ultrasound images and tools overlays on a display 230.

Example system 2 for image guidance permits image fusion of 3D image data with ultrasound data, without the customarily required interactions associated with registration, such as manually defining landmarks, identifying markers that have to present in pre-operative data, and similar steps. Unlike other navigation systems, the proposed invention does not require the presence of a separate reference or sensing base unit, and does not need additional setup steps beyond the observation of surfaces or surface features by the one or more cameras 100.

Illustrative Computer System

Figure 11:
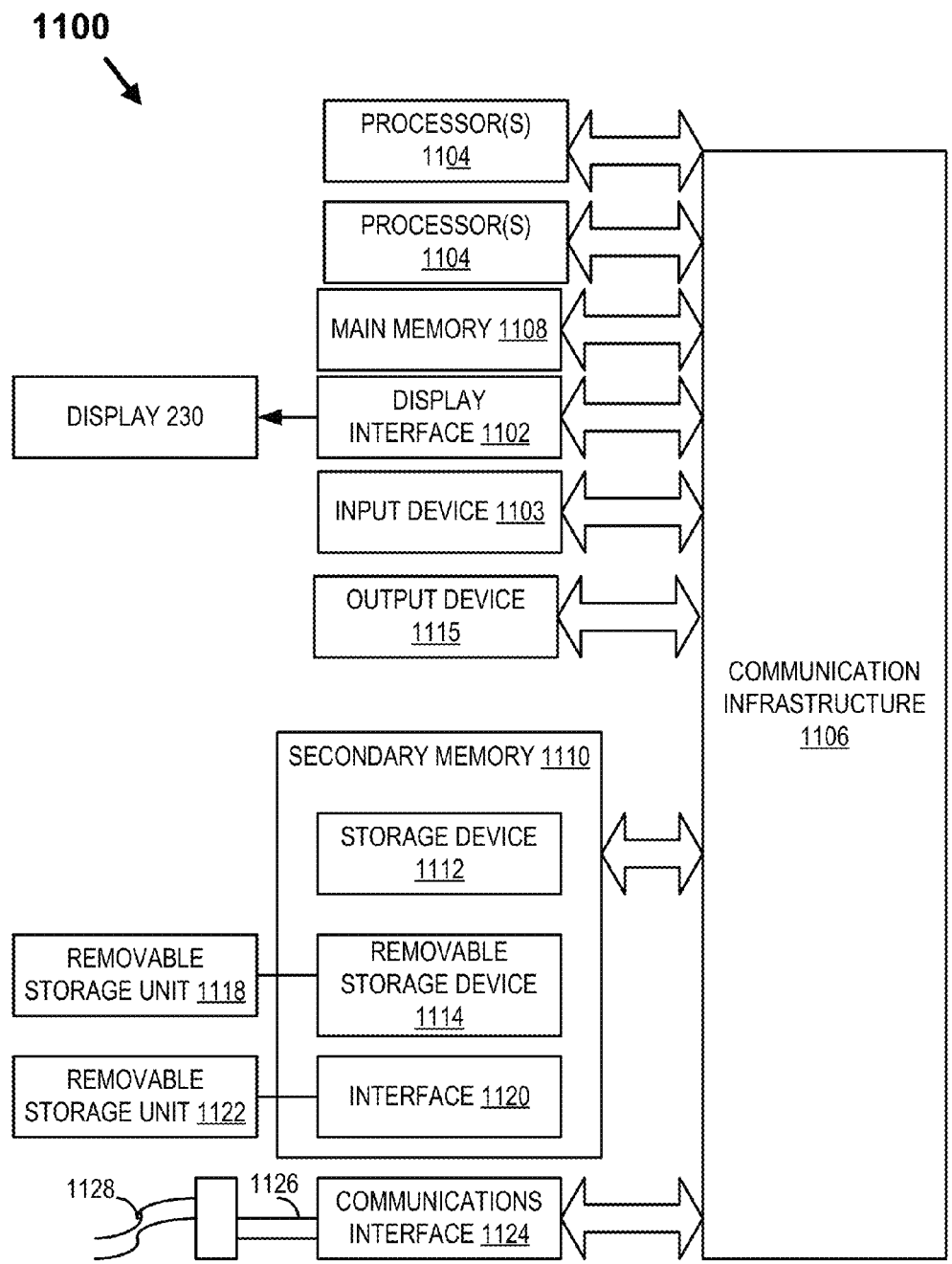
FIG. 11 depicts an illustrative computer system that may be used in implementing an illustrative embodiment of the present invention.

FIG. 11 depicts an illustrative computer system that may be used in implementing an illustrative embodiment of the present invention. Specifically, FIG. 11 depicts an illustrative embodiment of a computer system 1100 that may be used in computing devices such as, e.g., but not limited to, standalone or client or server devices. FIG. 11 depicts an illustrative embodiment of a computer system that may be used as client device, or a server device, etc. The present invention (or any part(s) or function(s) thereof) may be implemented using hardware, software, firmware, or a combination thereof and may be implemented in one or more computer systems or other processing systems. In fact, in one illustrative embodiment, the invention may be directed toward one or more computer systems capable of carrying out the functionality described herein. An example of a computer system 1100 is shown in FIG. 11, depicting an illustrative embodiment of a block diagram of an illustrative computer system useful for implementing the present invention. Specifically, FIG. 11 illustrates an example computer 1100, which in an illustrative embodiment may be, e.g., (but not limited to) a personal computer (PC) system running an operating system such as, e.g., (but not limited to) MICROSOFT® WINDOWS® NT/98/2000/XP/Vista/Windows 7/Windows 8, etc. available from MICROSOFT® Corporation of Redmond, Wash., U.S.A. or an Apple computer or tablet executing MAC® OS, OS X, or iOS from Apple® of Cupertino, Calif., U.S.A., or a computer running a Linux or other UNIX derivative. However, the invention is not limited to these platforms. Instead, the invention may be implemented on any appropriate computer system running any appropriate operating system. In one illustrative embodiment, the present invention may be implemented on a computer system operating as discussed herein. An illustrative computer system, computer 1100 is shown in FIG. 11. Other components of the invention, such as, e.g., (but not limited to) a computing device, a communications device, a telephone, a personal digital assistant (PDA), an iPhone, an iPad, a Surface, and Android device, a 3G/4G wireless device, an LTE device, a wireless device, a personal computer (PC), a handheld PC, a laptop computer, a smart phone, a mobile device, a netbook, a handheld device, a portable device, an interactive television device (iTV), a digital video recorder (DVR), client workstations, thin clients, thick clients, fat clients, proxy servers, network communication servers, remote access devices, client computers, server computers, peer-to-peer devices, routers, web servers, data, media, audio, video, telephony or streaming technology servers, etc., may also be implemented using a computer such as that shown in FIG. 11. In an illustrative embodiment, services may be provided on demand using, e.g., an interactive television device (iTV), a video on demand system (VOD), via a digital video recorder (DVR), and/or other on demand viewing system. Computer system 1100 and/or parts of computer system 1100 may be used to implement the network, processing device, and/or components as described in FIGS. 1-8, such as for example imaging processing unit 110, handheld unit 160, display 230, and/or one or more cameras 100.

The computer system 1100 may include one or more processors, such as, e.g., but not limited to, processor(s) 1104. The processor(s) 1104 may be connected to a communication infrastructure 1106 (e.g., but not limited to, a communications bus, cross-over bar, interconnect, or network, etc.). Processor 1104 may include any type of processor, microprocessor, or processing logic that may interpret and execute instructions (e.g., for example, a field programmable gate array (FPGA)). Processor 1104 may comprise a single device (e.g., for example, a single core) and/or a group of devices (e.g., multi-core processors or graphics/parallel processors). The processor 1104 may include logic configured to execute computer-executable instructions configured to implement one or more embodiments. The instructions may reside in main memory 1108 or secondary memory 1110. Processors 1104 may also include multiple independent cores, such as a dual-core processor or a multi-core processor. Processors 1104 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Computer system 1100 may include a display interface 1102 that may forward, e.g., but not limited to, graphics, text, and other data, etc., from the communication infrastructure 1106 (or from a frame buffer, etc., not shown) for display on the display unit 230 as described above. The display unit 230 may be, for example, an LCD or other screen for displaying data (e.g., a mobile phone or tablet screen). Output may also be provided as sound through a speaker.

The computer system 1100 may also include, e.g., but is not limited to, a main memory 1108, random access memory (RAM), and a secondary memory 1110, etc. Main memory 1108, random access memory (RAM), and a secondary memory 1110, etc., may be a computer-readable medium that may be configured to store instructions configured to implement one or more embodiments and may comprise a random-access memory (RAM) that may include RAM devices, such as Dynamic RAM (DRAM) devices, flash memory devices, Static RAM (SRAM) devices, etc.

The secondary memory 1110 may include, for example, (but is not limited to) a hard disk drive or solid-state drive as storage device 1112 and/or a removable storage drive 1114, representing a floppy diskette drive, a magnetic tape drive, an optical disk drive, a compact disk drive CD-ROM, flash memory, etc. The removable storage drive 1114 may, e.g., but is not limited to, read from and/or write to a removable storage unit 1118 in a well-known manner. Removable storage unit 1118, also called a program storage device or a computer program product, may represent, e.g., but is not limited to, a floppy disk, magnetic tape, optical disk, compact disk, etc. which may be read from and written to removable storage drive 1114. As will be appreciated, the removable storage unit 1118 may include a computer usable storage medium having stored therein computer software and/or data.

In alternative illustrative embodiments, secondary memory 1110 may include other similar devices for allowing computer programs or other instructions to be loaded into computer system 1100. Such devices may include, for example, a removable storage unit 1122 and an interface 1120. Examples of such may include a program cartridge and cartridge interface (such as, e.g., but not limited to, those found in video game devices), a removable memory chip (such as, e.g., but not limited to, an erasable programmable read only memory (EPROM), or programmable read only memory (PROM) and associated socket, and other removable storage units 1122 and interfaces 1120, which may allow software and data to be transferred from the removable storage unit 1122 to computer system 1100. Main memory 1109 and/or secondary memory 1110 may contain, at least, non-transitory instructions for performing the workflows described in FIGS. 9-10, for example.

Computer 1100 may also include an input device 1103 which may include any mechanism or combination of mechanisms that may permit information to be input into computer system 1100 from, e.g., a user. Input device 1103 may include logic configured to receive information for computer system 1100 from, e.g. a user. Examples of input device 1103 may include, e.g., but not limited to, a mouse, pen-based pointing device, or other pointing device such as a digitizer, a touch sensitive display device, and/or a keyboard or other data entry device (none of which are labeled). Other input devices 1103 may include, e.g., but not limited to, a biometric input device, a video source, an audio source, a microphone, an inertial sensor such as an accelerometer or a gyroscope, a magnetometer, a web cam, a video camera, and/or other cameras 100.

Computer 1100 may also include output devices 1115 which may include any mechanism or combination of mechanisms that may output information from computer system 1100. Output device 1115 may include logic configured to output information from computer system 1100. Embodiments of output device 1115 may include, e.g., but not limited to, display 230, and display interface 1102, including displays, printers, speakers, cathode ray tubes (CRTs), plasma displays, light-emitting diode (LED) displays, liquid crystal displays (LCDs), printers, vacuum florescent displays (VFDs), surface-conduction electron-emitter displays (SEDs), field emission displays (FEDs), etc. Computer 1100 may include input/output (I/O) devices such as, e.g., (but not limited to) input device 1103, communications interface 1124, cable 1128 and communications path 1126, etc. These devices may include, e.g., but are not limited to, a network interface card, and/or modems.

Communications interface 1124 may allow software and data to be transferred between computer system 1100 and external devices.

In this document, the terms "computer program medium" and "computer readable medium" may be used to generally refer to media such as, e.g., but not limited to, removable storage drive 1114, a hard disk or solid-state disk installed in storage device 1112, flash memories, removable discs, non-removable discs, etc. In addition, it should be noted that various electromagnetic radiation, such as wireless communication, electrical communication carried over an electrically conductive wire (e.g., but not limited to twisted pair, CAT5, etc.) or an optical medium (e.g., but not limited to, optical fiber) and the like may be encoded to carry computer-executable instructions and/or computer data that embodiments of the invention on e.g., a communication network. These computer program products may provide software to computer system 1200. It should be noted that a computer-readable medium that comprises computer-executable instructions for execution in a processor may be configured to store various embodiments of the present invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic.

Further, repeated use of the phrase "in one embodiment," or "in an illustrative embodiment," do not necessarily refer to the same embodiment, although they may. The various embodiments described herein may be combined and/or features of the embodiments may be combined to form new embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

In a similar manner, the term "processor" may refer to any device or portion of a device that processes electronic data from registers and/or memory to transform that electronic data into other electronic data that may be stored in registers and/or memory. A "computing platform" may comprise one or more processors.

Embodiments may be embodied in many different ways as a software component. For example, it may be a stand-alone software package, or it may be a software package incorporated as a "tool" in a larger software product, such as, for example, a scientific modeling product. It may be downloadable from a network, for example, a website, as a stand-alone product or as an add-in package for installation in an existing software application. It may also be available as a client-server software application, or as a web-enabled software application. It may also be part of a system for detecting network coverage and responsiveness. A general purpose computer may be specialized by storing programming logic that enables one or more processors to perform the techniques indicated herein and the steps of, for example.

Embodiments of the present invention may include apparatuses for performing the operations herein. An apparatus may be specially constructed for the desired purposes, or it may comprise a general purpose device selectively activated or reconfigured by a program stored in the device.

While various embodiments of the present invention have been described above, it should be understood that they have been presented by way of example only, and not limitation. Thus, the breadth and scope of the present invention should not be limited by any of the above-described illustrative embodiments, but should instead be defined only in accordance with the following claims and their equivalents.

We claim:

1. A system for image guidance comprising:
   an image processing system;
   a first imaging module, including one or more cameras, in communication with the image processing system, wherein the image processing system is configured to:
   receive secondary image data from a second imaging device;
   segment said secondary image data to determine a first surface of interest;

receive real-time imaging data from the first imaging module, wherein the real-time imaging data from the one or more cameras includes images of one or more of: a second surface of interest, an anchor marker, wherein the anchor marker provides a point and an orientation of the surface, a plurality of early or late markers, and tools;

calculate a registration transform of the first surface of interest relative to the second surface of interest using one or more of: the anchor marker, the plurality of early or late markers, or the second surface;

calculate a tracking location of the first imaging module relative to the first surface of interest using one or more of: the anchor marker, the plurality of early or late markers, the second surface, or features on the second surface; and create an enhanced image by combining information from the real-time imaging data with corresponding information computed from secondary image data based on the location of the first imaging module.

2. The system of claim 1, further comprising:
a display in communication with the image processing system,
and wherein said image processing system is further configured to:
display the enhanced image on the display.

3. The system of claim 2, wherein the display comprises at least one of: a tablet or a smartphone.

4. The system of claim 2, wherein the image processing system is further configured to:
calculate a location of the first imaging module relative to the display using one or more of: a plurality of markers attached to the display or features of the display; and
create an enhanced image by combining information from the real-time imaging data with information from one or more corresponding secondary image segments based on the location of the first imaging module and the display.

5. The system of claim 2, wherein the image processing system is further configured to:
calculate, receive, or extract from secondary image data, a proposed location for placement of a late anchor marker on the first surface of interest; and
display, on the display, the first surface of interest and the proposed location for the late anchor marker, wherein the late anchor marker is placed on the second surface of interest based on the proposed location on the first surface of interest.

6. The system of claim 1, wherein the image processing system is configured to communicate with additional remote system components for one or more of: computation, data storage, or data transmission.

7. The system of claim 1, wherein the enhanced image includes combinations of one or more of: digitally reconstructed radiographs, multi-plane reconstructions, images from the tracked first imaging module and corresponding images computed from secondary image data, tools at locations calculated based on camera observations, and target locations received from one or more of: pre-defined targets from the secondary image data or directly from an operator.

8. The system of claim 1, wherein one or more early markers are included in the secondary image data, and wherein the image processing system is further configured to automatically segment the one or more early markers.

9. The system of claim 1, wherein one or more early second markers are included in the secondary image data, and wherein the image processing system is further configured to automatically compute correspondences between the one or more early second markers and the images of the plurality of early or late markers from the real-time imaging data from the first imaging module.

10. The system of claim 1, wherein one or more early markers are included in the secondary image data, wherein the image processing system is further configured to:
register the first surface of interest with the second surface of interest initially using early or late markers known on both the first and second surfaces of interest, and then to refine an initial registration using the second surface.

11. The system of claim 1, wherein the image processing system is further configured to:
calculate a deformation of the first surface of interest due to an observed or estimated deformation applied to one or more of: the second surface of interest, or to the plurality of early or late markers, said deformation being applied by one or more of: the first imaging module, a tool, or other objects in contact with the second surface of interest.

12. The system of claim 11, wherein the image processing system is further configured to:
receive a selection of a target locations from one or more of pre-selected targets in the secondary image data or directly from an operator; and
recalculate a positions of the targets based on the deformation applied to the first surface of interest.

13. The system of claim 11, wherein the image processing system is further configured to:
create an enhanced deformed image by combining information from the real-time imaging data with information from one or more corresponding secondary image segments based on the location of the first imaging module, while applying the calculated deformation to the information.

14. The system of claim 1, further comprising:
a sensing device, wherein the sensing device is configured to provide ongoing orientation and translation estimates of the sensing device if one or more of the plurality of early or late markers is not viewable by the one or more cameras.

15. The system of claim 14, wherein the sensing device comprises at least one of an accelerometer, gyroscope, or magnetometer.

16. The system of claim 14, wherein the sensing device is coupled to one or more of: the first imaging module or a display in communication with the image processing system.

17. The system of claim 1, wherein the image processing system is further configured to:
successively reconstruct the second surface of interest and relative locations of the plurality of early or late markers based on the received real-time imaging data.

18. The system of claim 1, wherein the image processing system is further configured to:
determine a poor configuration of the early or late markers based on one or more of: received images of the early or late markers, surface information extracted from secondary image data, secondary image data, or target locations;
calculate an improved configuration for late markers of the plurality of early or late markers, wherein the improved configuration is based on one or more of: locations of the anchor marker, locations of other early or late markers, images of the second surface of interest, secondary image data, or target locations; and
transmit the improved configuration.

19. The system of claim 1, wherein the anchor marker or plurality of early or late markers comprise at least one of:
self-identifying tags, multi-modality markers, marker strips, patterned sheets, patterned clothing, natural anatomical features, skin features, or hair.

20. The system of claim 1, wherein the first imaging module further includes one or more secondary sensors, the one or more secondary sensors including at least one of: an ultrasound probe, a SPECT probe, an oximeter, or an optical vessel visualization device.

21. The system of claim 20, wherein the one or more cameras are physically decoupled from the one or more secondary sensors.

22. The system of claim 1, wherein the one or more cameras comprise optical cameras, infrared cameras, UV-sensitive cameras, light field sensors, plenoptic cameras, or catadioptric cameras.

23. The system of claim 1, wherein the secondary image data comprises data from one or more of: a CT scan, a CBCT scan, an x-ray image, a fluoroscope image, an MRI scan, a PET scan, or a SPECT scan.

24. A navigation method comprising:
receiving, by one or more processors, secondary images from a second imaging device;
segmenting, by the one or more processors, said secondary images to determine a first surface of interest;
receiving, by the one or more processors, real-time imaging data from a first imaging module, including visual data from a camera, wherein the visual data includes images of one or more of: a second surface of interest, an image of an early or late anchor marker, and images of a plurality of early or late secondary markers;
registering, by the one or more processors, the first surface of interest with the second surface of interest using one of more of: an early or late anchor marker, the early or late secondary markers, or the second surface;
calculating, by the one or more processors, a location of the first imaging module relative to the first surface of interest using one or more of: the early or late anchor marker, the plurality of early or late secondary markers, or the second surface, or features of the second surface; and
creating, by the one or more processors, enhanced images by combining the real-time imaging data from the first imaging module with corresponding secondary images from the second imaging device based on the location of the first imaging module.

25. The navigation method of claim 24, further comprising:
displaying the enhanced images on a display.

26. The navigation method of claim 25, further comprising:
calculating, by the one or more processors, a location of the first imaging module relative to the display using one or more of: a plurality of markers attached to the display, or features of the display; and
creating, by the one or more processors, enhanced images by combining the real-time imaging data from the first imaging module with corresponding secondary images from the second imaging device based on the location of the first imaging module and the display; and
displaying the enhanced images on the display.

27. The navigation method of claim 24, further comprising:
calculating, by the one or more processors, a suggested location for placement of a late anchor marker on the first surface of interest; and
displaying, on a display, the first surface of interest and the suggested location for the late anchor marker.

28. The navigation method of claim 24, further comprising:
automatically segmenting early markers contained in the secondary image data.

29. The navigation method of claim 24, further comprising:
automatically computing correspondences between early markers contained in the secondary image data and the plurality of early or late secondary markers observed by the first imaging module.

30. The navigation method of claim 24, further comprising:
calculating a deformation of the first surface based on the real-time imaging data from the first imaging module or real-time visual data from the camera; and
modifying secondary images and targets based on the calculated deformation.

31. The navigation method of claim 30, further comprising:
segmenting, by the one or more processors, said modified secondary images to determine a modified first surface of interest; and
registering, by the one or more processors, the modified first surface of interest with the second surface of interest sequentially using one of more of: the early or late anchor marker, the plurality of early or late secondary markers, features on the second surface, or the second surface.

* * * * *